United States Patent
Lim et al.

(10) Patent No.: US 10,393,673 B2
(45) Date of Patent: Aug. 27, 2019

(54) DOOR INSPECTION SYSTEM FOR VEHICLE AND INSPECTION METHOD FOR THE SAME

(71) Applicants: Hyundai Motor Company, Seoul (KR); Kia Motors Corporation, Seoul (KR); Dasannewtech Co., Ltd., Incheon-si (KR); Daewoo Industry Co., Ltd., Anyang-si (KR)

(72) Inventors: Young Soo Lim, Hwaseong-si (KR); Jin Cheol Kim, Incheon (KR); Kang Jae Jo, Incheon (KR); Bum-Hun Jun, Uiwang-si (KR)

(73) Assignees: Hyundai Motor Company, Seoul (KR); Kia Motors Corporation, Seoul (KR); Dasannewtech Co., Ltd, Incheon-si (KR); Daewoo Industry Co., Ltd., Anyang-si (KR)

( * ) Notice: Subject to any disclaimer, the term of this patent is extended or adjusted under 35 U.S.C. 154(b) by 74 days.

(21) Appl. No.: 15/711,882

(22) Filed: Sep. 21, 2017

(65) Prior Publication Data
US 2018/0011032 A1    Jan. 11, 2018

Related U.S. Application Data

(62) Division of application No. 14/072,246, filed on Nov. 5, 2013, now Pat. No. 9,791,381.

(30) Foreign Application Priority Data

Nov. 16, 2012  (KR) .......................... 10-2012-0130287

(51) Int. Cl.
*G01N 21/95*    (2006.01)

(52) U.S. Cl.
CPC ................................ *G01N 21/9515* (2013.01)

(58) Field of Classification Search
CPC ................................................... G01N 21/9515
(Continued)

(56) References Cited

U.S. PATENT DOCUMENTS

| 4,226,536 A | 10/1980 | Dreyfus et al. |
| 2006/0163778 A1 | 7/2006 | Maziers |

(Continued)

FOREIGN PATENT DOCUMENTS

| CN | 101696943 A | 4/2010 |
| CN | 101957176 A | 1/2011 |

(Continued)

OTHER PUBLICATIONS

Yu Dan, "Auto-front Door Internal Plate Check Measuring Tool Design," *Tool Engineering*, vol. 42:8 (2008).

*Primary Examiner* — Yulin Sun
(74) *Attorney, Agent, or Firm* — Morgan, Lewis & Bockius LLP

(57) ABSTRACT

An inspection system for a vehicle includes a vision inspection device including a plurality of vision camera and a plurality of laser device which move along exterior and sides of a door, which will be inspected, and inspect segmented sections respectively, a hanger device clamping the hemmed door on a hanger frame, and a jig device which clamps the hanger frame of the hanger device, and moves the door toward the vision inspection device for the vision inspection device to inspect the door fixed to the hanger device.

4 Claims, 14 Drawing Sheets

(58) Field of Classification Search
USPC .......................................................... 348/92
See application file for complete search history.

(56) References Cited

U.S. PATENT DOCUMENTS

2009/0069937 A1* 3/2009 Battenberg ............. B25J 9/1694
　　　　　　　　　　　　　　　　　　　　　700/254
2012/0137490 A1* 6/2012 Kweon ................... B23K 31/02
　　　　　　　　　　　　　　　　　　　　　29/428

FOREIGN PATENT DOCUMENTS

| CN | 102485574 A | 6/2012 |
| DE | 10 2011 011 360 A1 | 8/2012 |
| JP | 61-093933 A | 5/1986 |
| JP | 06-148092 A | 5/1994 |
| JP | 2000-241147 A | 9/2000 |
| JP | 2002-082060 A | 3/2002 |
| JP | 2004-333356 A | 11/2004 |
| JP | 2005-291845 A | 10/2005 |

* cited by examiner

DOOR INSPECTION SYSTEM FOR VEHICLE AND INSPECTION METHOD FOR THE SAME

CROSS-REFERENCE TO RELATED APPLICATION

The present application is a divisional of U.S. patent application Ser. No. 14/072,246, filed Nov. 5, 2013, which claims priority of Korean Patent Application Number. 10-2012-0130287 filed Nov. 16, 2012, the entire contents of which applications are incorporated herein for all purposes by these references.

BACKGROUND OF INVENTION

Field of Invention

The present invention relates to an inspection system for a vehicle and an inspection method for the same. More particularly, the present invention relates an inspection system for a vehicle and an inspection method for the same which may inspect exterior quality of a door supplied to a corresponding process line with relatively short time and prevent the door with bad quality from being supplied to the process line.

Description of Related Art

Generally, a vehicle is manufactured by numerous assembling processes using about twenty to thirty thousands of parts.

In particular, a vehicle body is formed by a first assembling process such that vehicle body panels are produced in a press process, and each part of the vehicle body is then assembled in a vehicle body factory to form a vehicle body of a body-in-white (BIW) state.

The formed vehicle body undergoes a main body process for mounting side walls, a loop, a rear panel, etc. on the floor thereof, and then is painted in painting process. After that, an engine, a transmission, an interior, and an exterior are assembled in an outfitting process.

Each panel to be mounted on the vehicle body is fabricated by a press working, is mounted and fixed on a panel jig apparatus in a vehicle body assembly process and undergoes operations including assembling, welding, sealing, and hemming, and is then painted in a painting process.

Undergoing the manufacturing processes, for example, spacing, precision of size, curved shape and so on of a door are important factors of exterior quality of a vehicle.

In the related art, since complete inspections of doors supplied to vehicle body assemble lines require a lot of human resources and processes, and thus sampling inspection is generally implemented.

In the related art, since the door inspection is implemented after manufacturing of the door manually and thus complete inspections of doors is not possible practically.

Also, it is not possible to prevent the door with bad exterior quality from supplying into after process, and thus field claim is increased and corporate image is deteriorated.

Thus, solve the problem of bad exterior quality of the vehicle, the door must be inspected before further manufacturing processes, statistical management of exterior quality is required, and automatic inspection of the door on process line is required.

The information disclosed in this Background section is only for enhancement of understanding of the general background of the invention and should not be taken as an acknowledgement or any form of suggestion that this information forms the prior art already known to a person skilled in the art.

BRIEF SUMMARY

Various aspects of the present invention provide for an inspection system for a vehicle and an inspection method for the same which may inspect exterior quality of a door supplied to a corresponding process line with relatively short time and prevent the door with bad quality from being supplied to the process line, so that statistical management of exterior quality is possible and automatic inspection of the door on process line is possible.

An inspection system for a vehicle according to various aspects of the present invention may include a vision inspection device including a plurality of vision camera and a plurality of laser device which move along exterior and sides of a door, which will be inspected, and inspect segmented sections respectively, a hanger device clamping the hemmed door on a hanger frame, and a jig device which clamps the hanger frame of the hanger device, and moves the door toward the vision inspection device for the vision inspection device to inspect the door fixed to the hanger device.

The vision inspection device may include a first base frame, first moving units which are disposed both sides of the first base frame, and move a first sliding plate to left and right direction of the first base frame, a second moving unit which is disposed between the first moving units through at least one supporting beam on the first base frame, and moves a second sliding plate to left and right direction of the first base frame, a visual inspection unit, which is movable along left and right side of the first base frame on the second sliding plate of the second moving unit and inspects the exterior of the door, and side inspection units, which are movable along left and right direction of the first base frame on each first sliding plate of the first moving unit and movable along up and down direction by a vertical moving unit for inspecting both sides of the door.

The first moving unit may include a first rail housing which is disposed on the first base frame, and on which a first sliding plate is slidably connected, a first drive motor which is mounted within the first rail housing, and of which a rotation shaft is connected to a first ball screw, a first guide rail mounted on the first base frame through a first plate within the first rail housing, and a first rail block into which the first ball screw is inserted, and which is disposed on the first guide rail movable along the first ball screw by operation of the first drive motor, and the first rail block is connected to the first sliding plate.

The second moving unit may include a second rail housing which is disposed between the first moving units on the first base frame though at least one supporting beam, and on which a second sliding plate is slidably connected, a second drive motor which is mounted within the second rail housing, and of which a rotation shaft is connected to a second ball screw, a second guide rail mounted on the supporting beam through a second plate within the second rail housing, and a second rail block into which the second ball screw is inserted, and which is disposed on the second guide rail movable along the second ball screw by operation of the second drive motor, and the second rail block is connected to the second sliding plate.

The vertical moving unit may include a supporting post mounted on the first sliding plate, a third rail housing which is mounted to a side of the supporting post toward the first base frame, and on which a third sliding plate is slidably connected, a third drive motor which is mounted within the third rail housing, and of which a rotation shaft is connected to a third ball screw, a third guide rail mounted on the supporting post through a third plate within the third rail housing, and a third rail block into which the third ball screw is inserted, and which is disposed on the third guide rail movable along the third ball screw by operation of the third drive motor, and the third rail block is connected to the third sliding plate.

The side inspection unit may include a bracket mounted to the third sliding plate, and a camera housing which is mounted to the bracket, of which a side toward the side of the door is opened, and of which the vision camera and the laser device are disposed therein.

The vision camera may be mounted inclined at a predetermined angle with respect to the laser device irradiation direction.

The visual inspection unit may include a mounting frame mounted to an upper portion of the second sliding plate, and a housing which is mounted to the mounting frame, of which a plurality of mounting space are formed therein, and the vision camera and the laser device are disposed to mounting space respectively.

A side of the housing toward the exterior of the door may be opened and the housing is mounted inclined with respect to the mounting frame at a predetermined angle.

The each vision camera may be inclined at a predetermined angle with respect to the laser device irradiation direction.

The each vision camera and the laser device may be misaligned along length direction of the housing.

The hanger device may include at least one door damper formed to a front side of the hanger frame for clamping the door, protrude portions formed an upper and lower portion of the hanger frame, and an arm mounting portion formed to a side of the hanger frame for an arm of a robot to be connected thereto.

The jig device may include a second base frame disposed on a floor, rails mounted both sides of an upper portion of the second base frame, a moving plate which is movable left and right direction of the second base frame along the rails though the fourth rail block, an operating cylinder which is mounted on the second base frame, and is connected to a lower portion of the moving plate for moving the moving plate, a supporting frame mounted on the moving plate, and a clamping unit which is mounted to the supporting frame corresponding to each protrude portion of the hanger frame and clamps the protrude portion.

The clamping unit may include a locator which is mounted to the supporting frame for supporting a rear portion of the protrude portion of the hanger frame, a clamping unit cylinder which includes an operating rod and is hingedly connected to a rear portion of the locator, a clamper of which a side is hingedly connected to a front portion of the locator, and the clamper is hingedly connected to the operating rod of the clamping unit cylinder, and a pusher which is mounted to the clamper and pushes the front side of the protrude portion supported by the locator.

An inspection method of a door for a vehicle, which inspects exterior and sides of a hemmed door according to various aspects of the present invention, the inspection method may include (a) moving the door using a hanger device to be mounted on a jig device, setting a vision inspection device according to a door type, and determining whether inspection setting for the door is completed, (b) moving the door to the vision inspection device according to the setting state, scanning and measuring the exterior of the door, and determining whether quality of the door is normal, and (c) sorting the door according to the quality of the door, and moving the door.

The step (a) may include picking up the hemmed door and moving the door using the hanger device, clamping the hanger device to the jig device and outputting signals of the door type, setting the vision inspection device according to the door type signals, determining whether the inspection setting is completed, and if it is determined that the inspection setting is not completed, outputting abnormal signals, stopping inspection process, and returning for outputting signals of the door type.

The step (b) may include if the inspection setting for the door is completed, moving the door toward the vision inspection device using the jig device, scanning and measuring the exterior and sides of the door using the vision inspection device, and determining whether the size and exterior quality of the door scanned and measured using the vision inspection device is normal.

The step (c) may include if the size and exterior quality of the door scanned and measured using the vision inspection device is not normal, determining the door is bad and displaying the result, separating the hanger device where the door is clamped from the jig device and moving the door to a place for poor doors, if the size and exterior quality of the door scanned and measured using the vision inspection device is normal, determining the door is good and displaying the result, and separating the hanger device where the door is clamped from the jig device and moving the door to a place for good doors;

The methods and apparatuses of the present invention have other features and advantages which will be apparent from or are set forth in more detail in the accompanying drawings, which are incorporated herein, and the following Detailed Description, which together serve to explain certain principles of the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
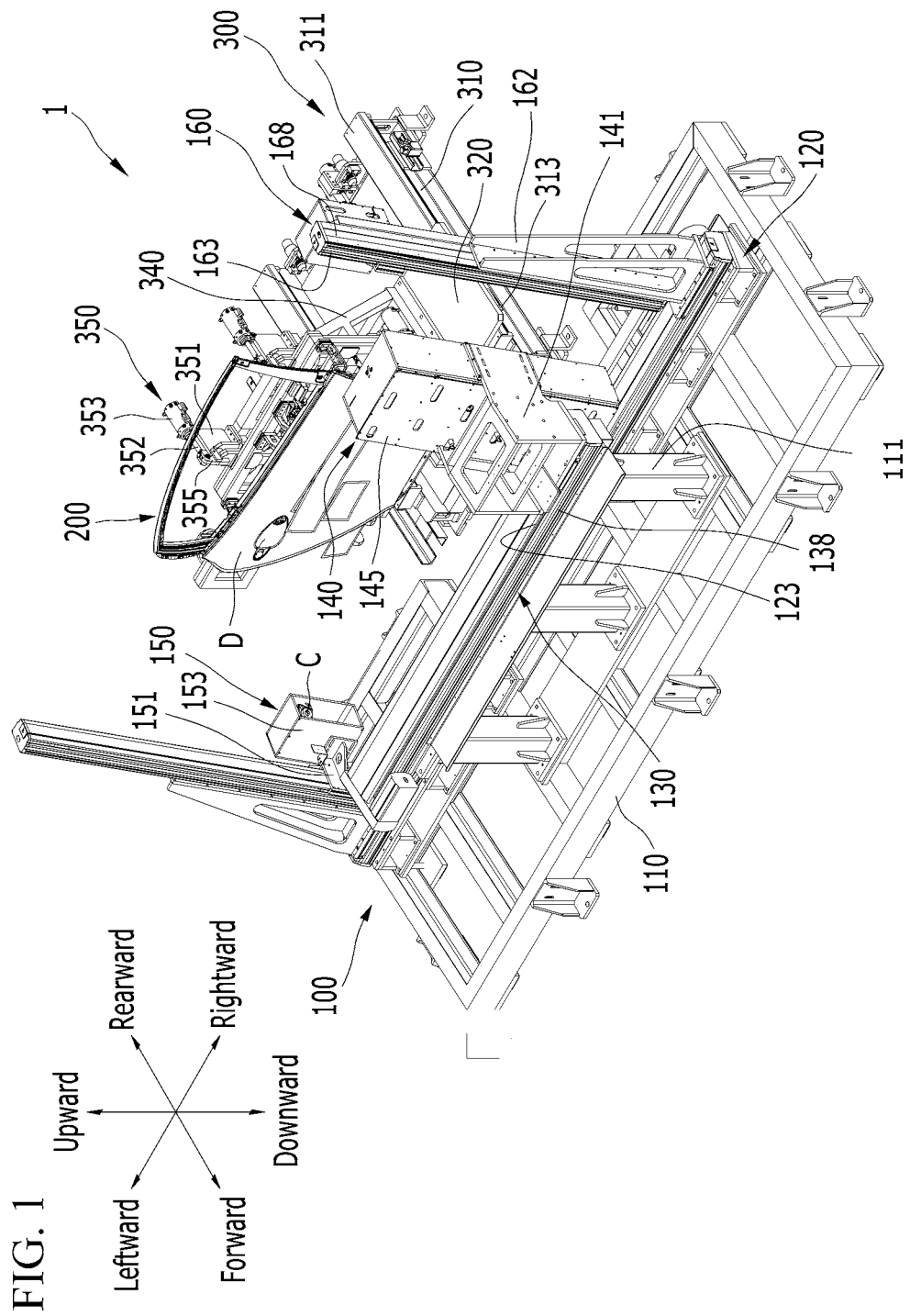
FIG. 1 is a perspective view of an exemplary inspection system for a vehicle according to the present invention.

FIG. 1 is a perspective view of an inspection system for a vehicle according to various embodiments of the present invention.

Referring to the drawing, an inspection system for a vehicle 1 according to various embodiments of the present invention may inspect exterior quality of a door D supplied to a corresponding process line with relatively short time and prevent the door with bad quality from being supplied to the process line using a vision inspection device 100, a hanger device 200 and a jig device 300, so that statistical management of exterior quality is possible and automatic inspection of the door on process line is possible.

The inspection system for a vehicle 1 according to various embodiments of the present invention includes the vision inspection device 100, the hanger device 200 and the jig device 300, and detailed elements will be described hereinafter.

Figure 2:
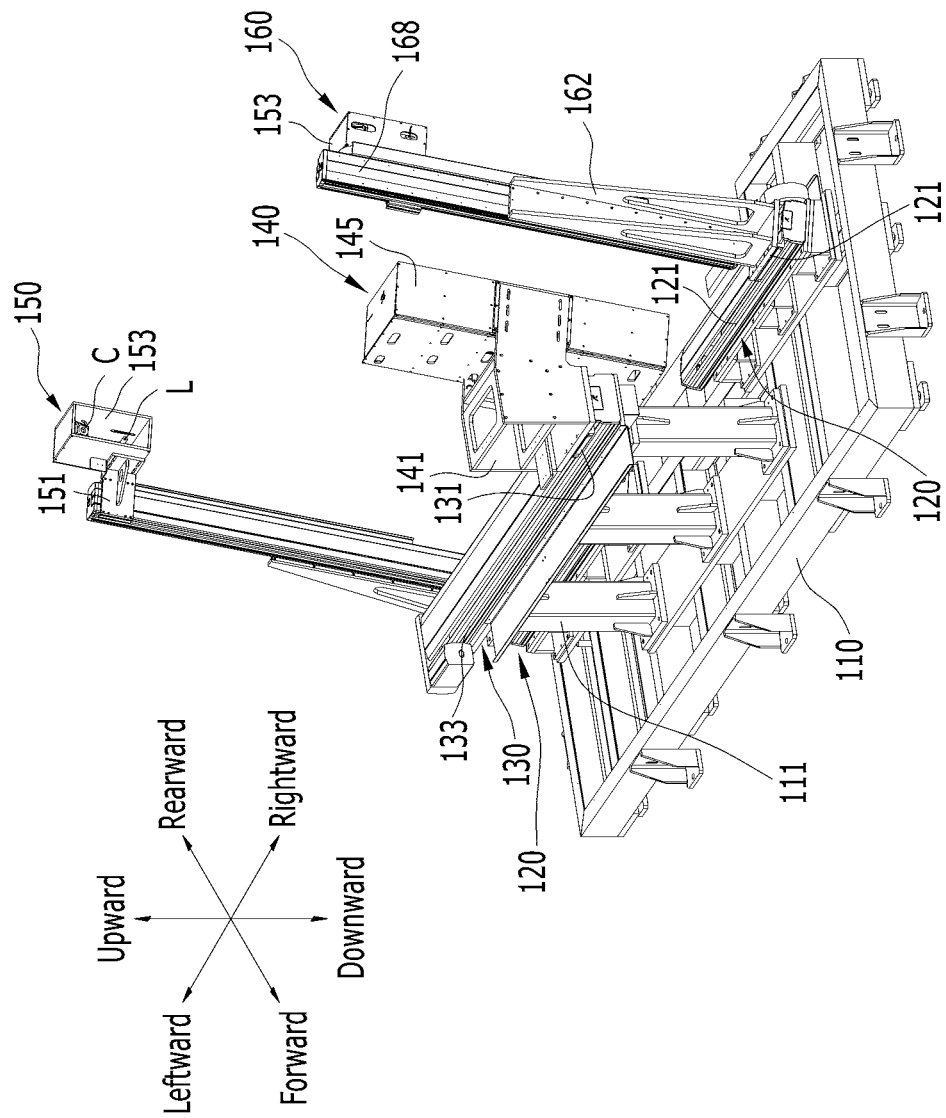
FIG. 2 is a perspective view of a vision inspection device applied to an exemplary inspection system for a vehicle according to the present invention.
Figure 3:
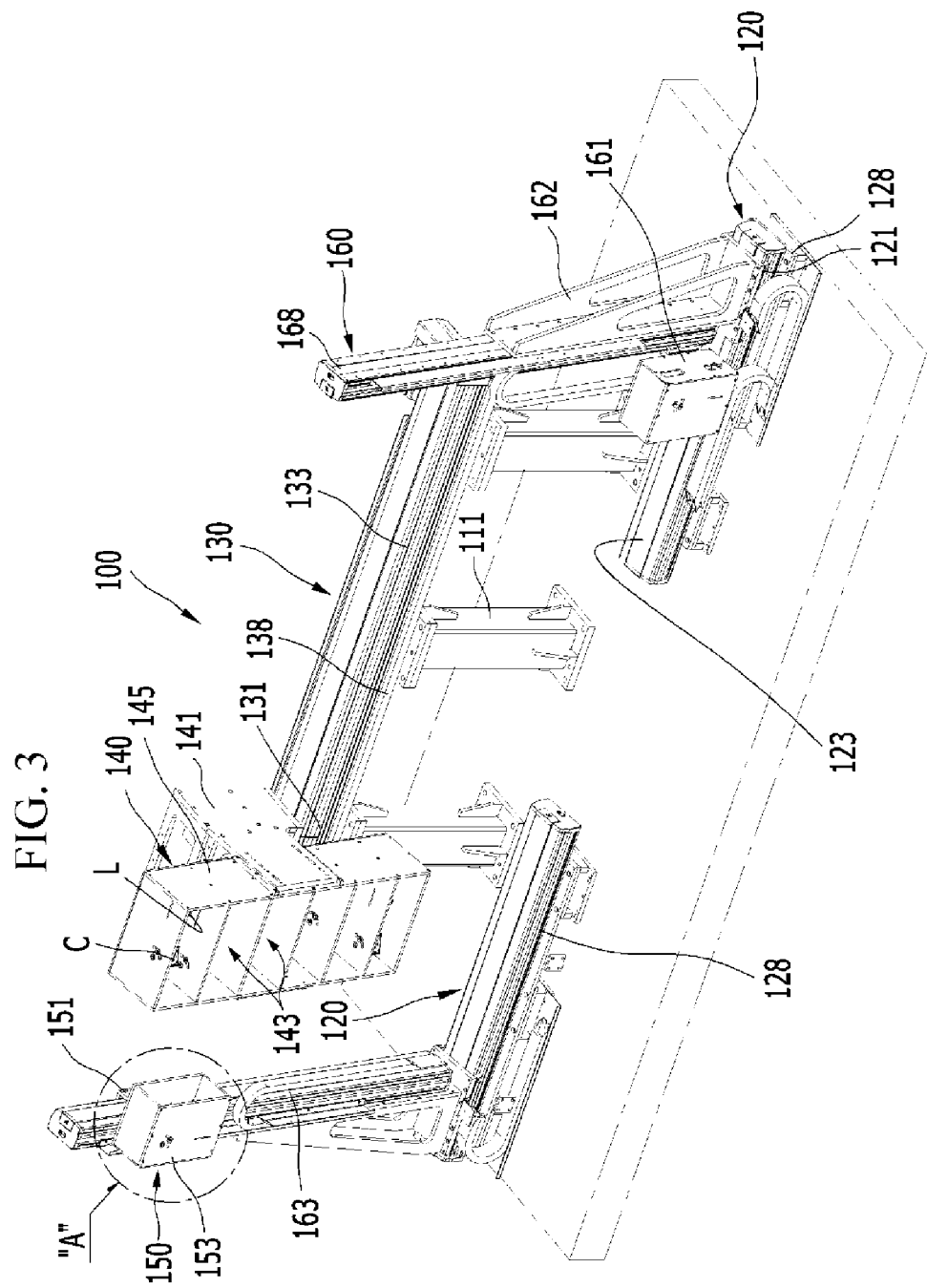
FIG. 3 is a rearward perspective view of a vision inspection device applied to an exemplary inspection system for a vehicle according to the present invention.

FIG. 2 is a perspective view of a vision inspection device applied to an inspection system for a vehicle according to various embodiments of the present invention, and FIG. 3 is a rearward perspective view of a vision inspection device applied to an inspection system for a vehicle according to various embodiments of the present invention.

In various embodiments, the vision inspection device 100, as shown in FIG. 2 and FIG. 3, inspects exterior and both sides of the door D by moving a plurality of vision camera C and a plurality of laser device L to inspect segmented sections.

The vision inspection device 100 includes a first base frame 110, a first moving unit 120, a second moving unit 130, a visual inspection unit 140 and side inspection units 150.

The first base frame 110 is mounted on a floor, and the first and second moving unit 120 and 130 are mounted thereon.

In various embodiments, the first moving units 120 are disposed on both sides of the first base frame 110 respectively and moves the first sliding plate 121 to left and right direction of the first base frame 110.

Figure 4:
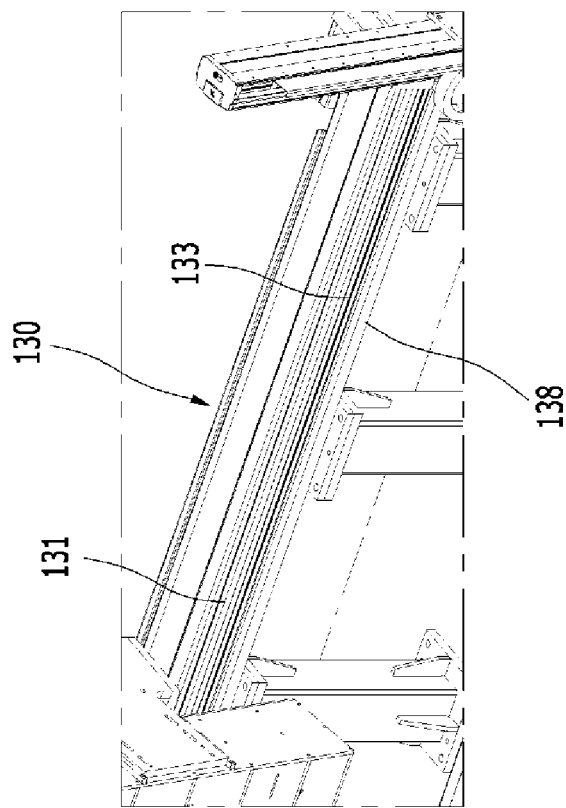
FIG. 4 and FIG. 5 are drawings showing a moving unit and a vertical moving unit applied to an exemplary vision inspection device according to the present invention.
Figure 5:
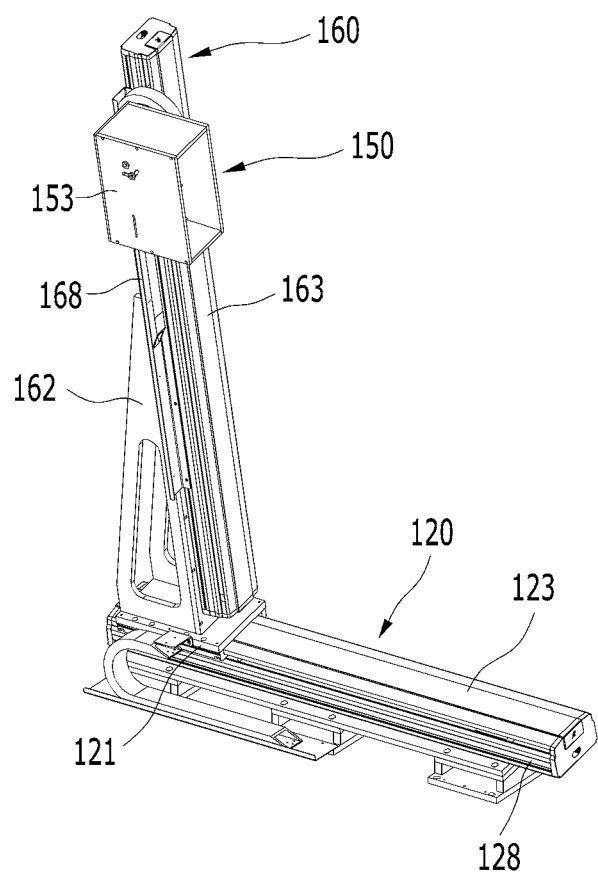
Figure 6:
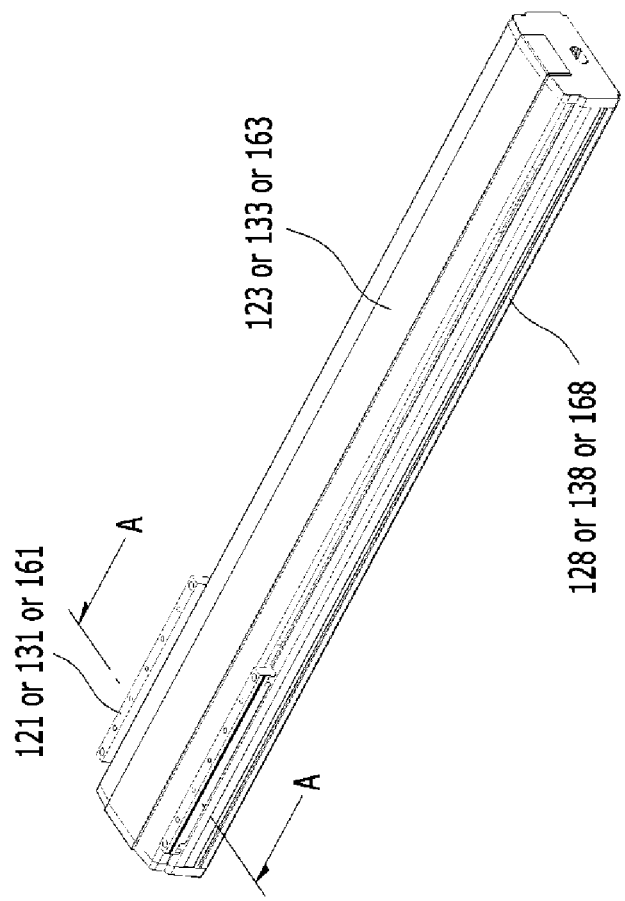
FIG. 6 is a perspective view of a moving unit and a vertical moving unit applied to an exemplary vision inspection device according to the present invention.
Figure 7:
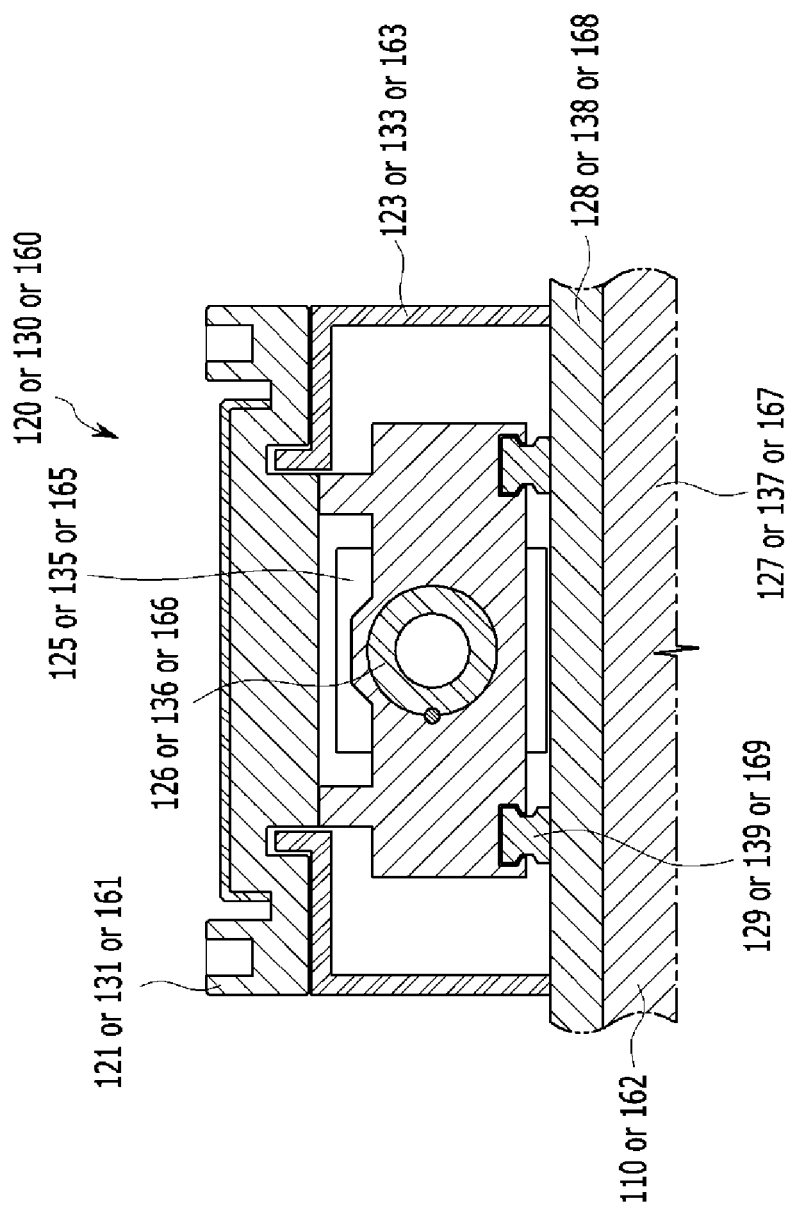
FIG. 7 is a cross-sectional view along line A-A of FIG. 6.

FIG. 4 and FIG. 5 are drawings showing a moving unit and a vertical moving unit applied to a vision inspection device of various embodiments of the present invention. FIG. 6 is a perspective view of a moving unit and a vertical moving unit applied to a vision inspection device of various embodiments of the present invention, FIG. 7 is a cross-sectional view along line A-A of FIG. 6.

The first moving unit 120, referring to FIG. 1 to FIG. 7, includes a first rail housing 123, a first drive motor 125, a first guide rail 127 and a first rail block 129.

The first rail housings 123 are disposed along left and right direction of the first base frame 110, and the first sliding plate 121 is slidably connected thereon.

The first drive motor 125 is mounted within the first rail housing 123 and a rotation shaft of which is connected to the first ball screw 126.

In various embodiments, the first guide rail 127 is disposed on the first base frame 110 through the first plate 128 within the first rail housing 123.

The first ball screw 126 is inserted into the first rail block 129, and the first rail block 129 is movable along the first guide rail 127 by the operation of the first drive motor 125 and is connected to the first sliding plate 121.

The first rail block 129 of the first moving unit 120 moves along the first guide rail 127 by forward or rearward rotation of the first drive motor 125, and simultaneously, the first sliding plate 121 connected with the first rail block 129 moves left or right direction of the base frame 110.

In various embodiments, the second moving unit 130 is disposed between the first moving units 120 through at least one supporting beam 111 on the first base frame 110, and moves a second sliding plate 131 to left and right direction of the first base frame 110.

In various embodiments of the present invention, since shape and constituent elements of the second moving unit 130 is similar to the first moving unit 120, and thus the second moving unit 130 will be described referring to FIG. 4 to FIG. 7.

Referring to the drawings, the second moving unit 130 includes a second rail housing 133, a second drive motor 135, a second guide rail 137 and a second rail block 139.

The second rail housing 133 between the first moving units 120 is mounted to the first base frame 110 though a plurality of supporting beam 111 and the second sliding plate 131 is slidably connected thereto.

The second drive motor 135 is mounted within the second rail housing 133 and a rotation shaft of which is connected to the second ball screw 136.

In various embodiments, the second guide rail 137 is disposed on the supporting beam 111 through the second plate 138 within the second rail housing 133.

The second ball screw 136 is inserted into the second rail block 139, and the second rail block 139 is movable along the second guide rail 137 on the second ball screw 136 by the operation of the second drive motor 135 and is connected with the second sliding plate 131.

The second rail block 139 of the second moving unit 130 moves along the second guide rail 137 by forward or rearward rotation of the second drive motor 135, and simultaneously, the second sliding plate 131 connected the second rail block 139 moves left or right direction of the base frame 110.

Figure 8:
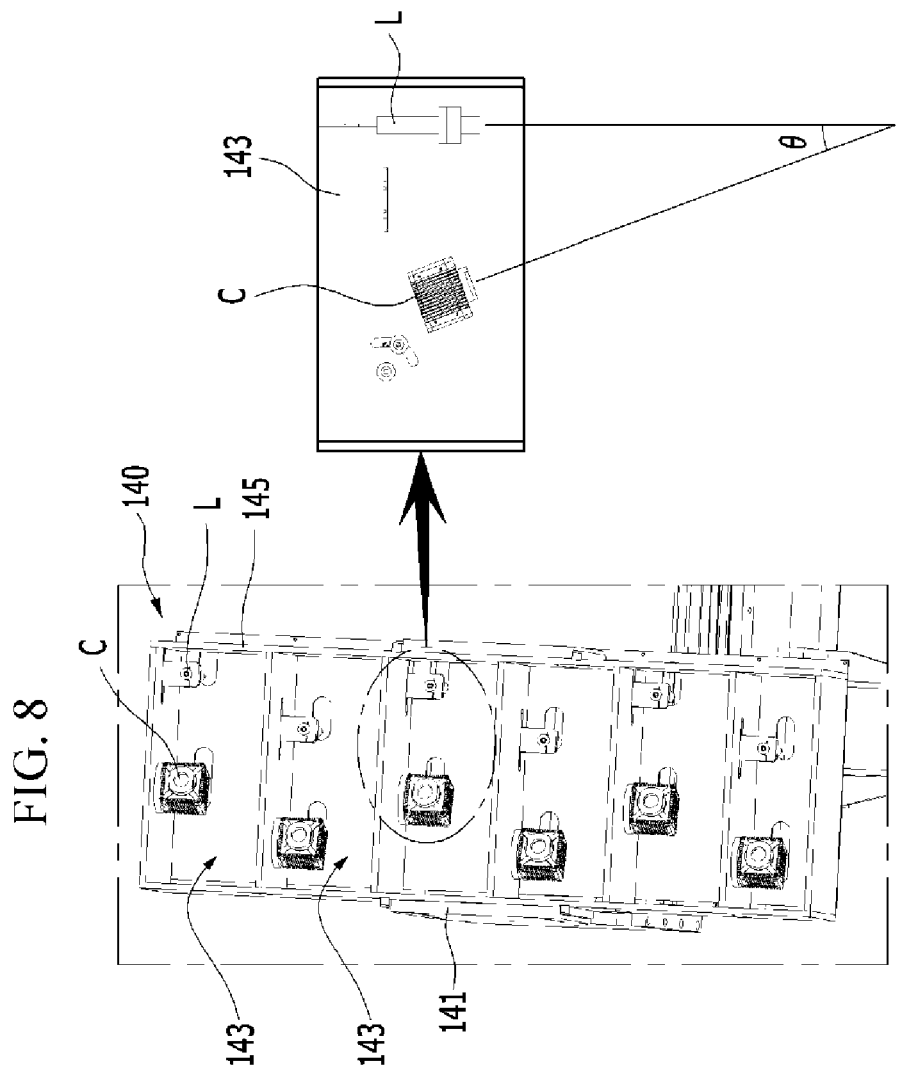
FIG. 8 is a drawing showing a visual inspection unit applied to an exemplary vision inspection device according to the present invention.

FIG. 8 is a drawing showing a visual inspection unit applied to a vision inspection device of various embodiments of the present invention.

Referring to the drawing, the visual inspection unit 140 is movable left or right direction of the first base frame 110 through the second sliding plate 131 of the second moving unit 130 and inspects or measures the exterior of the door D.

The visual inspection unit 140, referring to FIG. 2, FIG. 3 and FIG. 8, includes a mounting frame 141 and a housing 145.

The mounting frame 141 is mounted an upper portion of the second sliding plate 131.

The housing 145 is mounted to the mounting frame 141, and a plurality of mounting space 143 is formed therein along length direction thereof, and the vision camera C and the laser device L is mounted to the each mounting space 143 at a predetermined position.

A side of the housing 145, referring to FIG. 8, corresponding to the exterior of the door D is open, and the housing 145 is mounted at an incline with respect to the mounting frame 141 at a predetermined angle.

The vision camera C is mounted at an incline within the mounting space 143 with a predetermined angle with respect to the laser device L irradiation direction.

That is, the vision camera C is mounted at an incline with a predetermined angle θ with respect to the laser device L irradiation direction.

In this case, the predetermined θ is about 20°, for optimizing resolution and inspection speed of the vision camera C.

When the laser device L forms cross-sectional profile along vertical direction of the door D, the vision camera C takes 2D photographs of the laser, forms 3D image and then takes the cross-sectional profile to surfacization.

The vision camera C changes light intensity to voltage using Charge Coupled Device (CCD) sensor provided to a lens, expresses voltage as gray scale, and then transmits corresponding signal to a non-illustrated controller.

The visual inspection unit 140 moves along left and right direction of the door D by the operation of the second moving unit 130, and inspects or measures the door D using the vision camera C and the laser device L.

The each vision camera C and the laser device L is misaligned (not parallel) along length direction of the housing 145 within each mounting space 143.

Since the each vision camera C and the laser device L is misaligned (not parallel), the exterior of the door D may be divided and inspected respectively. So the inspection of the exterior quality of the door D may be implemented quickly.

The side inspection units 150 are movable along left and right direction of the first base frame 110 on each first sliding plate 121 of the first moving unit 120 and movable along up and down direction by a vertical moving unit 160 for inspecting both sides of the door D.

In various embodiments of the present invention, since shape and constituent elements of the vertical moving unit 160 is similar to the first moving unit 120, and thus the vertical moving unit 160 will be described referring to FIG. 4 to FIG. 7.

Referring to the drawings, the vertical moving unit 160 includes a supporting post 162, a third rail housing 163, a third drive motor 165, a third guide rail 167 and a third rail block 169.

The supporting post 162 is mounted to an upper portion of the first sliding plate 121.

The third rail housing 163 is mounted to a side of the supporting post 162 toward the first base frame 110, and a third sliding plate 161 is slidably connected thereon.

The third drive motor 165 is mounted within the third rail housing 163 and a rotation shaft of which is connected to the third ball screw 166.

The third guide rail 167 is disposed on the supporting post 162 through the third plate 168 within the third rail housing 163.

The third ball screw 166 is inserted into the third rail block 169, and the third rail block 169 is movable along the third guide rail 167 on the third ball screw 166 by the operation of the third drive motor 165 and is connected with the third sliding plate 161.

The third rail block 169 of the vertical moving unit 160 moves along the third guide rail 167 by forward or rearward rotation of the third drive motor 165, and simultaneously, the third sliding plate 161 connected with the third rail block 169 moves up and down direction of the base frame 110.

Figure 9:
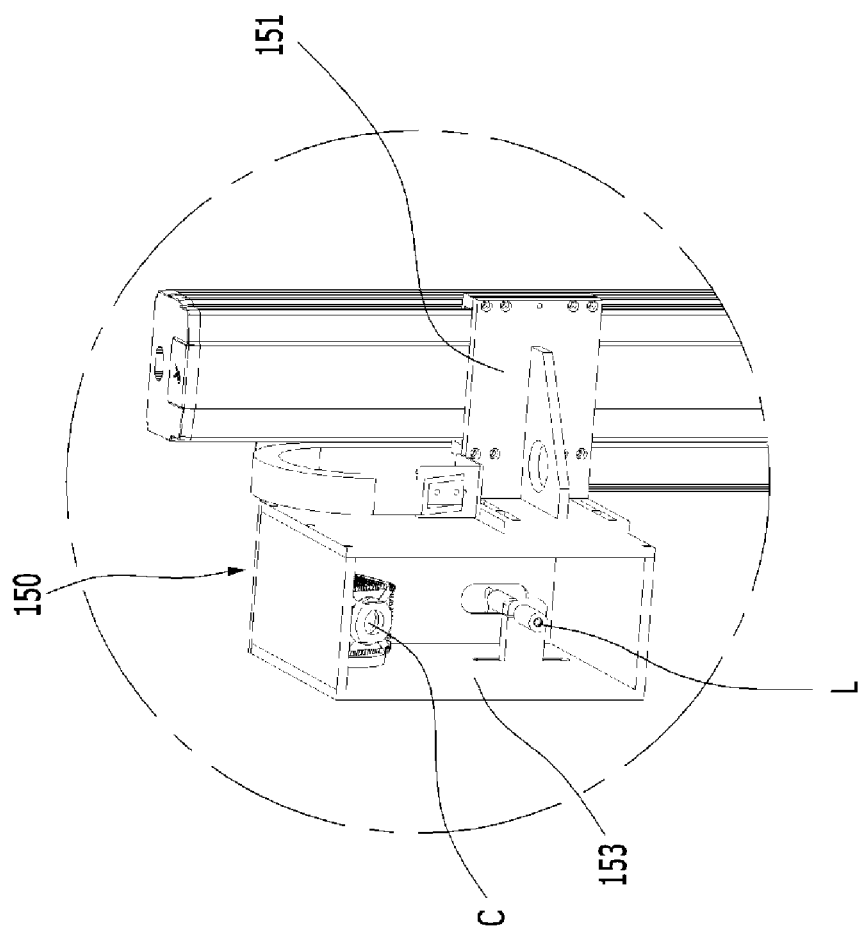
FIG. 9 is a drawing showing a side inspection unit applied to an exemplary vision inspection device according to the present invention.

FIG. 9 is a drawing showing a side inspection unit applied to a vision inspection device of various embodiments of the present invention.

Meanwhile, in various embodiments of the present invention, the side inspection unit 150, as shown in FIG. 9, includes a bracket 151 mounted to the third sliding plate 161 and a camera housing 153 which is mounted to the bracket 151, of which aside toward the side of the door D is opened, and of which the vision camera C and the laser device L are disposed therein.

As same as the visual inspection unit 140, the vision camera C is mounted at an incline at a predetermined angle with respect to the laser device L irradiation direction.

In this case, the predetermined θ is about 20°, for optimizing resolution and inspection speed of the vision camera C.

When the laser device L forms cross-sectional profile along vertical direction of the door D, the vision camera C takes 2D photographs of the laser, forms 3D image and then takes the cross-sectional profile to surfacization.

The operation of the side inspection unit 150 is similar to the above described visual inspection unit 140, and thus detailed description will be omitted.

Figure 10:
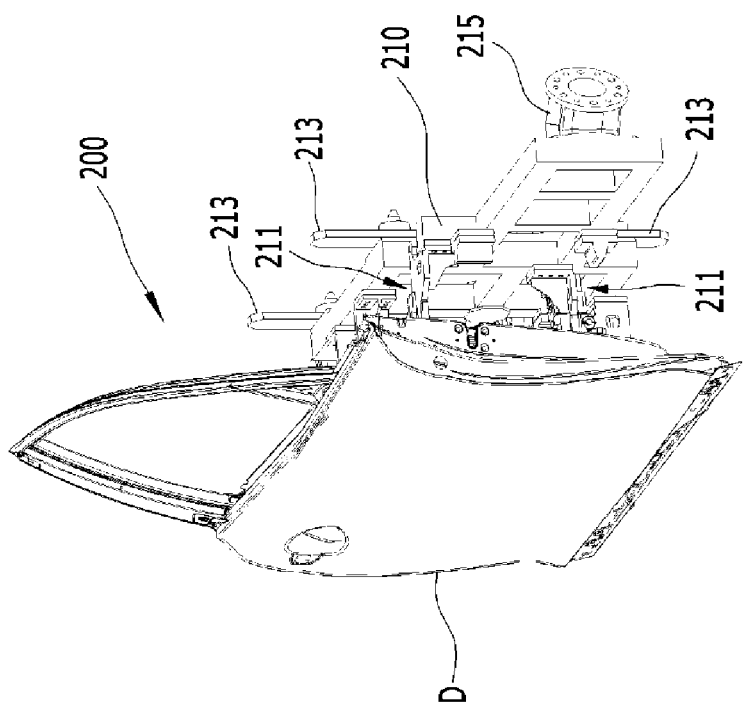
FIG. 10 is a drawing showing a hanger device applied to an exemplary inspection system for a vehicle according to the present invention.

FIG. 10 is a drawing showing a hanger device applied to an inspection system for a vehicle according to various embodiments of the present invention.

In the drawings, the hanger device 200 clamps the hemmed door D inspection object of the vision inspection device 100 using the hanger frame 210 and is movable by a robot.

The hanger device 200 includes at least one door clamper 211 mounted to a front side of the hanger frame 210 for clamping the door D, protrude portions 213 formed an upper and lower portion of the hanger frame 210, and an arm mounting portion 215 formed to a side of the hanger frame 210 for an arm of a robot to be connected thereto.

Figure 11:
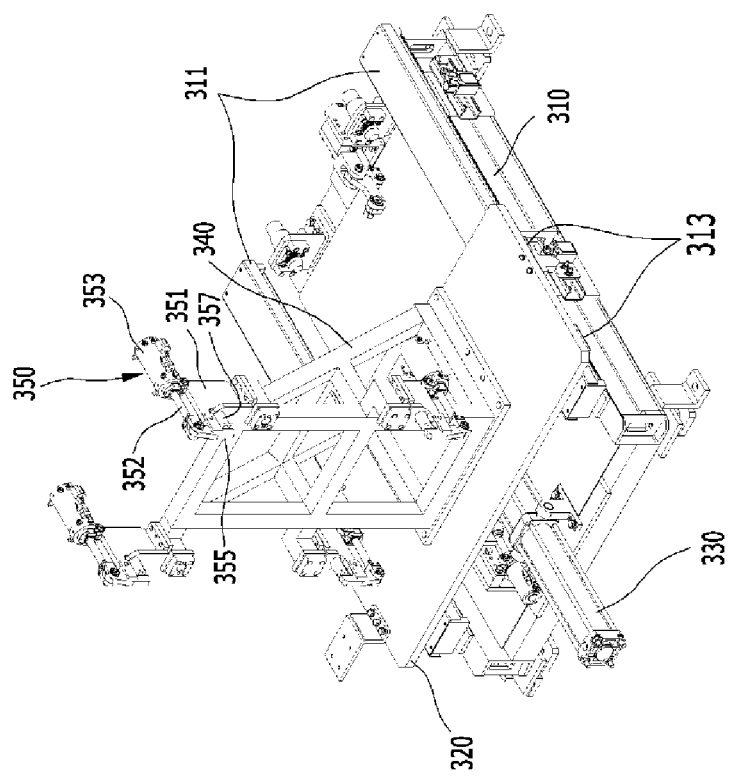
FIG. 11 is a drawing showing a jig device applied to an exemplary inspection system for a vehicle according to the present invention.
Figure 12:
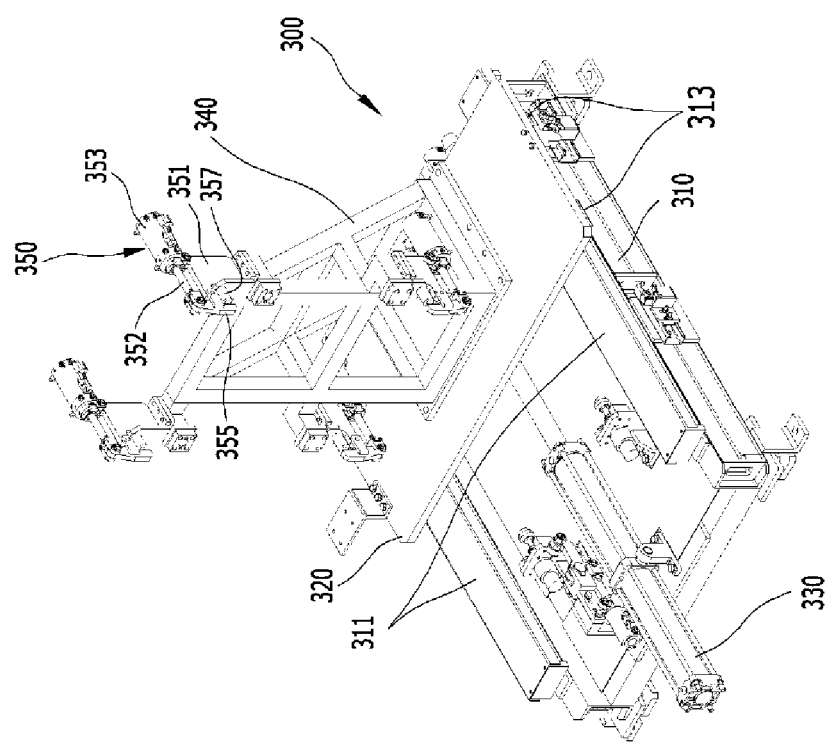
FIG. 12 is a drawing showing operations of a jig device applied to an exemplary inspection system for a vehicle according to the present invention.

FIG. 11 is a drawing showing a jig device applied to an inspection system for a vehicle according to various embodiments of the present invention, and FIG. 12 is a drawing showing operations of a jig device applied to an inspection system for a vehicle according to various embodiments of the present invention.

Referring to the drawings, the jig device 300 clamps the hanger frame 210 of the hanger device 200, and moves the door D toward the vision inspection device 100 for the vision inspection device 100 to inspect the door D fixed to the hanger device 200.

The jig device 300 includes a second base frame 310, a rail 311, a moving plate 320, an operating cylinder 330, a supporting frame 340 and a clamping unit 350.

The second base frame 310 is disposed on a floor rearward of the first base frame 110.

The rails 311 are disposed on both side of an upper portion of the second base frame 310 along length direction.

The moving plate 320 is movable left and right direction of the second base frame 310 along the rails 311 though the fourth rail block 313.

The operating cylinder 330 including a non-illustrated operating rod is mounted on the second base frame 310, and is connected to a lower portion of the moving plate 320 for moving the moving plate 320 by supplying or releasing of operation fluid.

The supporting frame 340 is mounted to an upper portion of the moving plate 320 and is movable by the moving plate 320 when the operating cylinder 330 is operated to forward or rearward.

The clamping unit 350 is mounted to the supporting frame 340 corresponding to each protrude portion 213 of the hanger frame 210 and clamps the protrude portion 213.

The clamping unit 350 includes a locator 351, a clamping unit cylinder 353, a damper 355 and a pusher 357.

The locator 351 is mounted to the supporting frame 340 for supporting a rear portion of the protrude portion 213 of the hanger frame 210.

The clamping unit cylinder 353 includes an operating rod 352 and is hingedly connected to a rear portion of the locator 351.

A side of the damper 355 is hingedly connected to a front portion of the locator 351, and the damper 355 is hingedly connected to the operating rod 352 of the clamping unit cylinder 353.

The pusher 357 is mounted to the damper 355 and pushes the front side of the protrude portion 213 supported by the locator 351.

The moving plate 320 of the jig device 300, as shown in FIG. 12, positions rearward of the second base frame 310 by the forward operation of the operating cylinder 330 before the hanger device 200 clamping the door D is clamped thereto.

The hanger unit 200 clamping the door D is moved by a robot to the jig device 300, and then as shown in FIG. 11, the operating cylinder 330 is operated rearward to move the moving plate 320 to forward of the second base frame 310 after clamping the hanger frame 210 by the clamping unit 350.

Thus, the door D is moved to the vision inspection device 100 positioned forward of the second base frame 310.

Hereinafter, operations of the inspection system for a vehicle according to various embodiments of the present invention will be described.

Figure 13:
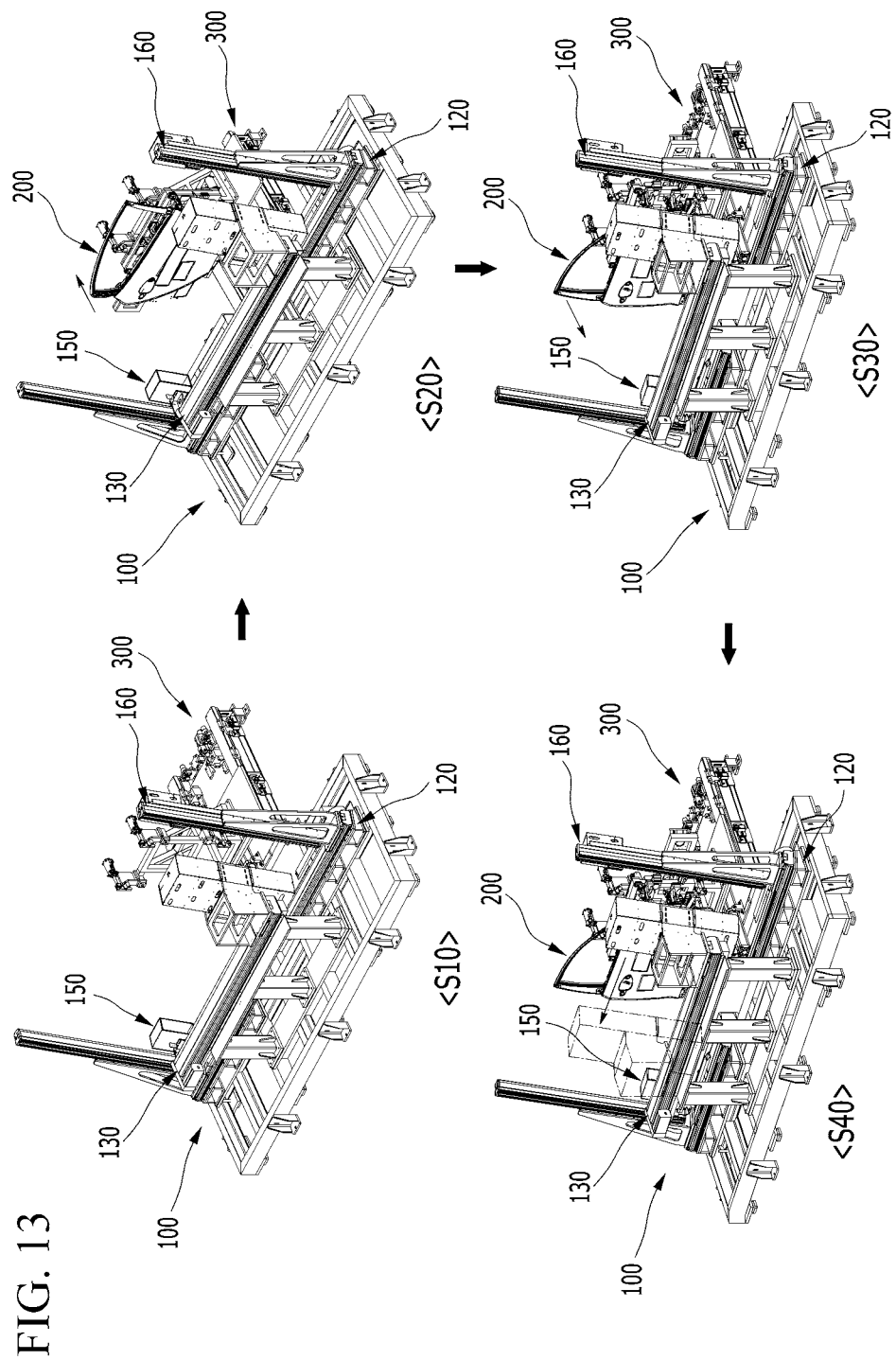
FIG. 13 is a drawing showing operations of an exemplary inspection system for a vehicle according to the present invention.
Figure 14:
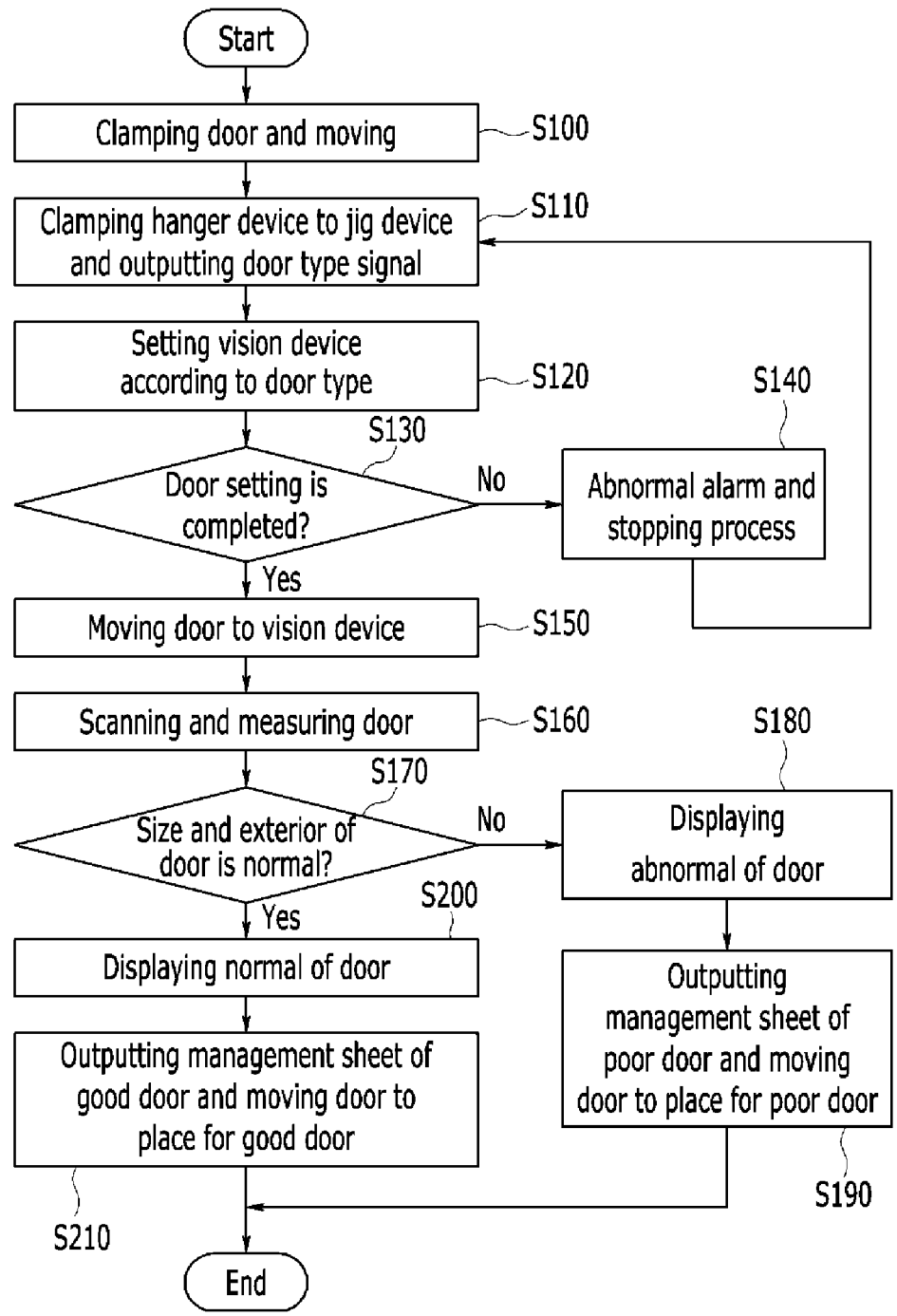
FIG. 14 is a flow chart of an exemplary inspection method for a vehicle according to the present invention.

FIG. 13 is a drawing showing operations of an inspection system for a vehicle according to various embodiments of the present invention, and FIG. 14 is a flow chart of an inspection method for a vehicle according to various embodiments of the present invention.

An inspection method of a door for a vehicle, which inspects exterior and sides of a hemmed door according to various embodiments of the present invention includes (a) moving the door D using the hanger device 200 to be mounted on the jig device 300, setting the vision inspection device 100 according to the door type (door model), and determining whether inspection setting for the door D is completed, (b) moving the door D to the vision inspection device 100 according to the setting state, scanning and measuring the exterior of the door D, and determining whether quality of the door D is normal, and (c) sorting the door D according to the quality of the door D, moving the door D, and closing the processes.

The hanger device 200 clamps the hemmed door D, is moved by the robot, and set on the jig device 300 (S100).

As shown in FIGS. 12 and S10 of FIG. 13, the moving plate 320 is moved rearward of the second base frame 310 by the operation of the operating cylinder 330 and also the supporting frame 340 is moved rearward of the second base frame 310.

After movement of the hanger device 200 clamping the door D to the jig device 300, the jig device 300, as shown in S20 of FIG. 13, clamps the hanger frame 210 of the hanger device 200 by the operation of the clamping unit 350, and then transmits type or model signal of the door D to a non-illustrated controller (S110).

The controller sets the vision inspection device 100 according to the output signal at the step S110 (S120), and then determines the setting for inspection of the door D (S130).

If it is determined that the inspection setting for the door D is not completed at the vision inspection device 100, outputting abnormal signals, and stopping inspection process (S140), and then returning to the step (S110) for outputting signals of the door type.

If the inspection setting for the door D is completed, the jig device 200, as shown in S30 of FIG. 13, moves the door D toward the vision inspection device by moving the hanger frame 210 clamped to the supporting frame 340 forward of the second base frame 310 according to the operation of the operating cylinder 330 (S150).

Then the controller, as shown in S40 of FIG. 13, controls the operations of the first and second moving unit 120 and 130 and the vertical moving unit 160 so that the visual inspection unit 140 and the side inspection unit 150 scans and measuring the exterior and sides of the door D (S160).

In this case, the laser device L of the visual inspection unit 140 and the side inspection unit 150 forms cross-sectional profile along vertical direction of the door D, the vision camera C takes 2D photographs of the laser, forms 3D image and then takes the cross-sectional profile to surfacization.

Then the controller analyses the image signal scanned and measured by the each vision camera C of the vision inspection device 100, outputs the inspection result and compares with a predetermined value for determining the size and exterior quality of the door D is normal (S170).

If the size and exterior quality of the door D scanned and measured using the vision inspection device 100 is not normal, the controller determines the door D is bad and displaying the result (S180).

Then the controller outputs management sheets of the poor door D, separates the hanger device 200 where the door D is clamped from the jig device 300 and moves the door D to a place for poor doors (S190), and then the process is completed. After that the process is repeated the inspection for the hemmed door D.

On the other hand, if the size and exterior quality of the door D scanned and measured using the vision inspection device 100 is normal, the controller determines the door D is good and displaying the result (S200).

Then the controller outputs management sheets of the poor door D, separates the hanger device 200 where the door D is clamped from the jig device 300 and moves the door D to a place for good doors (S210), and then the process is completed. After that the process is repeated the inspection for the hemmed door D.

As described above, the inspection system for a vehicle according to various embodiments of the present invention may inspect exterior quality of a door D supplied to a corresponding process line with relatively short time and prevent the door D with bad quality from being supplied to the process line using the vision inspection device 100, the hanger device 200 and the jig device 300, so that statistical management of exterior quality is possible and automatic inspection of the door on process line is possible.

That is, after inspection of the door D, the door D is supplied to the post process, and thus statistical management of exterior quality of the door D may be possible.

Since the vision inspection device 100 inspects segmented sections of the door D without integration or combination of the segmented sections, and thus fast inspection may be possible and man power for inspection may be reduced.

Also, it is possible to prevent the door with bad exterior quality from supplying into post process, and thus field claim may be reduced and corporate image is enhanced.

For convenience in explanation and accurate definition in the appended claims, the terms upper or lower, front or rear, and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An inspection method of a door for a vehicle for inspecting an exterior and sides of a hemmed door, the inspection method comprising:
   (a) moving the door using a hanger device to be mounted on a jig device, setting a vision inspection device according to a door type, and determining whether inspection setting for the door is completed;
   (b) moving the door to the vision inspection device according to the setting state, scanning and measuring the exterior of the door, and determining whether quality of the door is normal; and
   (c) sorting the door according to the quality of the door, and moving the door.

2. The inspection method of claim 1, wherein the step (a) comprises:
   picking up the hemmed door and moving the door using the hanger device;
   clamping the hanger device to the jig device and outputting signals of the door type;
   setting the vision inspection device according to the door type signals;
   determining whether the inspection setting is completed; and
   if it is determined that the inspection setting is not completed, outputting abnormal signals, stopping inspection process, and returning for outputting signals of the door type.

3. The inspection method of claim 1, wherein the step (b) comprises:
   if the inspection setting for the door is completed, moving the door toward the vision inspection device using the jig device;
   scanning and measuring the exterior and sides of the door using the vision inspection device; and
   determining whether the size and exterior quality of the door scanned and measured using the vision inspection device is normal.

4. The inspection method of claim 1, wherein the step (c) comprises:
   if the size and exterior quality of the door scanned and measured using the vision inspection device is not normal, determining the door is bad and displaying the result;
   separating the hanger device where the door is clamped from the jig device and moving the door to a place for poor doors;
   if the size and exterior quality of the door scanned and measured using the vision inspection device is normal, determining the door is good and displaying the result; and
   separating the hanger device where the door is clamped from the jig device and moving the door to a place for good doors.

* * * * *